United States Patent

Gehre et al.

[11] Patent Number: 5,976,890
[45] Date of Patent: Nov. 2, 1999

[54] REDUCTION FURNACE PROCESS FOR QUANTITATIVE DEUTERIUM DETERMINATION IN HYDROGEN CONTAINING SAMPLES

[75] Inventors: Matthias Gehre, Leipzig; Reiner Höfling, Engelsdorf; Peter Kowski, Leipzig, all of Germany

[73] Assignee: UFZ-Umweltforschungszentrum Leipzig-Halle GmbH, Germany

[21] Appl. No.: 08/817,104
[22] PCT Filed: Oct. 2, 1995
[86] PCT No.: PCT/EP95/03889
  § 371 Date: Jun. 6, 1997
  § 102(e) Date: Jun. 6, 1997
[87] PCT Pub. No.: WO96/11397
  PCT Pub. Date: Apr. 18, 1996

[30] Foreign Application Priority Data

Oct. 5, 1994 [DE] Germany ............ P 44 37 120

[51] Int. Cl.⁶ ............................................. G01N 33/18
[52] U.S. Cl. ............... 436/144; 436/39; 436/155; 436/159; 436/173; 436/174; 436/177; 436/181; 95/89; 96/105; 250/288; 422/78
[58] Field of Search ............ 73/864.81, 864.86; 96/105; 95/89; 250/288; 436/39, 159, 144, 155, 173, 174, 177, 181; 422/68.1, 81, 78

[56] References Cited

U.S. PATENT DOCUMENTS

4,332,591  6/1982  Oi et al. .
4,916,313  4/1990  Hall et al. .

OTHER PUBLICATIONS

Begley et al., Rapid Commun. Mass Spectrom. 91996), 10(8), 969–973, 1996.
Morse et al., Chemical Geology (Isotope Geoscience Section), 107 (1993) 147–158, 1993.

*Primary Examiner*—Jan Ludlow
*Attorney, Agent, or Firm*—Londa and Traub LLP

[57] ABSTRACT

The invention relates to a method for the quantitative determination of deuterium in samples containing hydrogen, and to a reduction oven for reducing gaseous or liquid substances containing hydrogen, which may be coupled directly to an isotope ratio mass spectrometer (IRMS), thereby permitting an online-coupled, reliable deuterium determination which can be automatized.

7 Claims, 3 Drawing Sheets

REDUCTION FURNACE PROCESS FOR QUANTITATIVE DEUTERIUM DETERMINATION IN HYDROGEN CONTAINING SAMPLES

The invention relates to a method for the quantitative determination of deuterium in samples containing hydrogen, and to a reduction oven for reducing gaseous or liquid substances containing hydrogen, which may be coupled directly to an isotope ratio mass spectrometer (IRMS), thereby permitting an online-coupled, reliable deuterium determination which can be automatized.

BACKGROUND

In deuterium determination using an IRMS, various sample-chemical methods for generating hydrogen are known. In each case, the mass-spectrometric isotope analysis is performed using hydrogen gas which must be generated from each sample either by reduction or isotope exchange between water and hydrogen. Most widely known are offline methods involving separation of sample chemistry and measurement. The hydrogen gas is liberated by means of reducing agents such as iron, manganese, zinc, uranium and chromium, where no satisfactory results are achieved when using iron and manganese.

According to the well-known zinc method (Coleman M. L., Sherpherd T. J., Durham J. J., Rouse J. E., Moore G. R., Anal. Chem. 1982, 54, 993–995, and Kendall C. and Coplen T. B., Anal. Chem. 1985, 57, 1437–1440; and Tanweer A., Anal. Chem. 1990, 62, 2158–2160 and Vennemann T. W. and O'Neil J. R., Chem. Geol. (Isot. Geosci. Sect.) 1993, 103, 227–234), the reduction of water using zinc is effected at about 400° C. in ampoules or in a circulation system. Depending on the method, the sample quantity required is 5–70 mg of pure water.

Disadvantageously, only zinc made using a special production process provides satisfactory results. If the water contains contaminations (oil, salt etc.), this method cannot be applied. In addition, the isotope ratio is distorted by the solubility of hydrogen in zinc.

Furthermore, the use of uranium as reducing agent is well-known. Water is reduced by uranium at various temperatures (400–800° C.) in a special apparatus. The sample quantity is analogous to that in the above-mentioned zinc method (Bigeleisen J., Perlmann M. L., H. C. Anal. Chem. 1952, 24, 1356–1357, and GB patent 904,165, and GSF Jahresbericht 1987, 217–225).

Disadvantageously, specific temperature conditions must be maintained precisely because the solubility of hydrogen in uranium is temperature-dependent. Deviations in temperature result in irreversible formation of uranium hydride (distorting the isotope ratio). The use of contaminated water (oil, salt etc.) is not possible.

Reduction using chromium has also been suggested (Rolle W., Hübner H., Fresenius Z., Anal. Chemie 232 [1967] 328, and Runge A., Isotopenpraxis 16 [1980] 2). The reduction of water and other hydrogen-containing substances by chromium is effected at temperatures between 700 and 1000° C. in ampoules or special apparatus. The sample quantity required is 5 mg of water or an amount of hydrogen from another hydrogen-containing substance, which is equivalent to said quantity of water.

Likewise, online methods using coupling to the IRMS are known. According to Horita, J. Chem. Geol. (Isot. Geosci. Sect.) 1988, 72, 89–94, and in J. Chem. Geol. (Isot. Geosci. Sect.) 1989, 79, 107–112, and Horita J., Ueda A., Mizukami K. and Takatori I., Appl. Radiat. Isot. 40 (1989) 9, 801–805), an isotope exchange method is known. In this method, the isotope equilibrium between a water sample and hydrogen gas is established using a platinum catalyst, and the sample is directly introduced into the IRMS.

This method is disadvantageous in that large quantities of sample (20 ml of pure water) are required, constant temperature ($\leq 0.03°$ C.) during exchange must be ensured because of the temperature dependence of the isotope separation factor, and a great deal of time is required in sample preparation, so that this method is difficult to handle and has found only minor use.

According to ZFI-Mitteilungen 37 (1981), pp. 49–52, and GB patent 904,165, and GSF-Jahresberichte 1985–1987, it is also well-known to use the reduction process for online procedures. The coupled methods of sample preparation suggested so far, involving mass spectrometer and IRMS, respectively, use uranium as reducing agent. However, these methods permit only reduction of water. Other hydrogen-containing substances cannot be reduced. In addition, the set-up of equipment is not uncomplicated, larger quantities of sample are required, and commercially available autosamplers cannot be used because of these sample quantities.

Thus, the method described in ZFI-Mitteilungen 37 (1981), pp. 49–52, involves complete evaporation of a water sample in a pre-connected vessel and subsequent reduction of a part of the water vapor on uranium in a post-connected apparatus, before the gas to be measured is introduced into the mass spectrometer to determine the isotope ratio (D/H) (cf., FIG. 16).

In addition to the problems of using uranium as reducing agent, which were already mentioned, the measuring procedure of determining the isotope ratio by integrating the area of the measured signals in this latter case can also be referred to as disadvantageous.

SUMMARY OF THE INVENTION

Therefore, it was the object of the invention to provide a method for the quantitative determination of deuterium using online coupling of sample preparation and IRMS, which permits measurement of minute sample quantities of gaseous and liquid substances containing hydrogen, is exceedingly simple in the set-up of equipment, and has high measuring precision (reproducibility of values). The method should allow automatization.

The object of the invention is attained by means of a method in accordance with claims 1 through 6, using a new reduction oven using reduction oven for reducing hydrogen-containing samples and which is directly coupled to a mass spectrometer. The reduction oven is constructed of a high temperature-resistant hydrogen-impermeable material and has an injection unit with a septum for introducing the sample. A capillary directly connects the injection unit with a reaction chamber containing a reducing agent. Importantly, there are no expansion vessels connected in between the injection unit and the reaction chamber. A joint pipe connects the reaction chamber to the mass spectrometer.

The reaction chamber is confined by a temperature-resistant material permeable for the hydrogen gas. The reduction oven may be constructed where the high temperature-resistant hydrogen-impermeable material is quartz glass. The injection unit is configured for injection of 1 $\mu$l of water, or another hydrogen-containing sample corresponding in its hydrogen content to an amount of 1 $\mu$l of water. The capillary has a length which totally prohibits isotope fractionation during sample evaporation, which would distort the measurement result. The injection unit operates ideally at a temperature of about 150° C.

Further, the capillary has an internal diameter of between about 0.6–1.0 mm, and preferably is about 0.8 mm and the length of the capillary is between substantially 50–100 mm. The reaction chamber is also designed to have a capacity that at least 100 water samples of 1 μl each or an amount of other hydrogen-containing samples corresponding in their hydrogen content to 100 water samples can be passed using a single charge of reducing agent. The reaction chamber has a length which ranges between 50–60 mm and an internal diameter of between substantially 15–20 mm, and the joint pipe has a length of between substantially 60–100 mm, preferably about 90 mm. The reducing agent within the reaction chamber can be any number of select reducing agents, but chromium is preferred. Optionally, a catalyst may also be added thereto. The material confining the reaction chamber is quartz wool.

DETAILED DESCRIPTION

Figure 1:
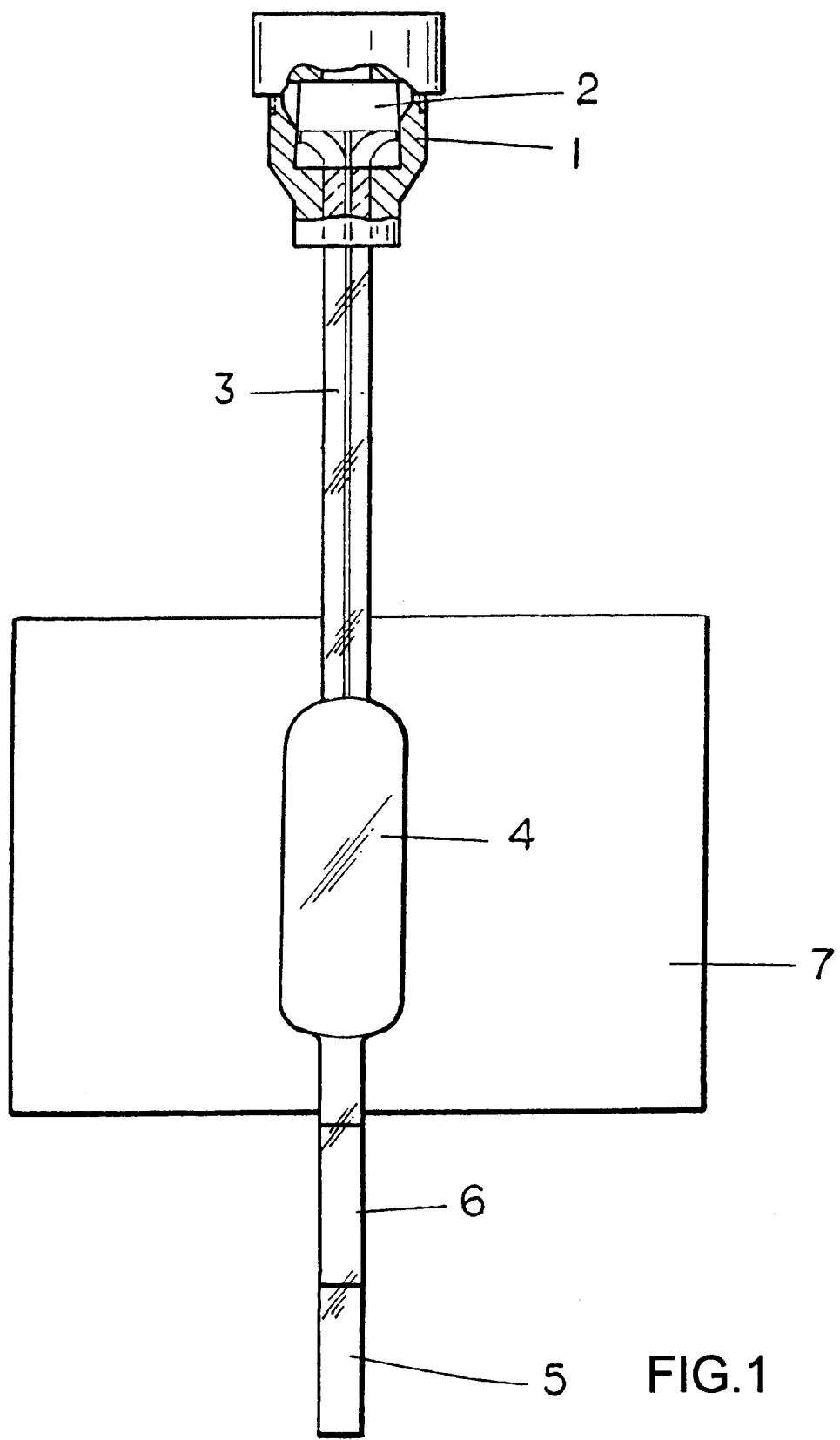
FIG. 1 is a view of the reduction oven of the invention with an exterior heating device.

The reduction oven of the invention is illustrated in FIG. 1, together with the exterior heating device 7 which is used to heat the reduction oven and must have a design permitting maintenance of a constant reduction temperature in the reaction chamber 4 of the oven. Preferably, an infrared oven or an electric heater may be employed.

In a particularly preferred embodiment of the method according to the invention, the reduction oven of the invention is charged with chromium powder having a grain size of from 0.16 to 0.3 mm, evacuated and heated at a temperature ranging from 700 to 1100° C.

After reaching the reduction temperature in the reaction chamber 4 and a temperature of about 150° C. at the injection unit, the sample (1 μl of water or hydrogen equivalent) is injected with a vacuum-tight microliter syringe into the reduction oven through the injection unit 1 sealed with a septum 2 from external air. The sample evaporating explosively is reduced and, due to the pressure difference between the reduction oven and the bellow of the inlet element, the hydrogen formed will flow into the mass spectrometer. Following pressure balancing (about 20 s), the bellow inlet valve is closed, and the measurement of the isotope ratio D/H begins.

After each measurement, residues of the measured gas must be carefully pumped out of the reduction oven, the bellow and the mass spectrometer, which is achieved by pumping for about 5 minutes using the IRMS high-vacuum pump.

It was found that no memory effects occur both in the reduction oven and in the IRMS when complying with this procedure.

At the beginning of each measurement, the intensities of the mass 2 measured signals of the hydrogen gas from sample and standard in the IRMS are adjusted to the intensity ranges (predefined by the manufacturer of the IRMS device) by means of the bellows. Thereafter, the isotope ratio is measured in sample/standard alternation and the δD value of the sample is calculated.

The reduction of organic, hydrogen-containing substances sometimes requires a longer residence time in the reduction oven (up to 45 minutes in the case of methane) before reduction of the substance to hydrogen is complete. This period of time may be reduced considerably by including a catalyst in the reducing agent. In the case of methane, for example, the reaction time is reduced to 15 minutes when using nickel wool. Metals such as Ni, Co, Wo, Mo, or Pt may be used as catalysts. Preferably, the chromium/catalyst ratio is between 100:1 to 20:1.

Figure 2:
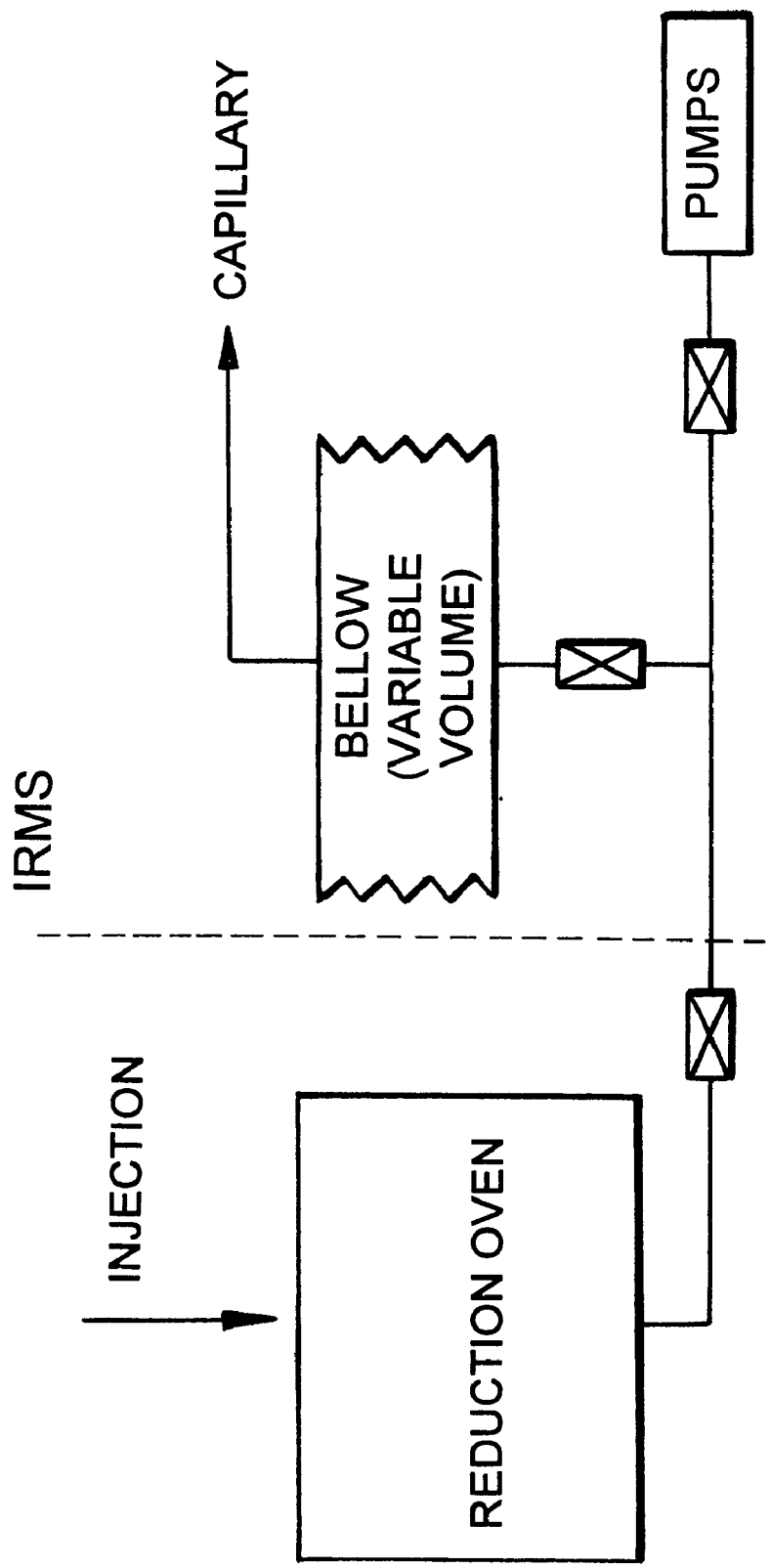
FIG. 2 is a schematic diagram of the online coupling of the invention between reaction oven and IRMS.

The schematic diagram of the online coupling of the invention between reaction oven and IRMS is shown in FIG. 2. Advantageously, sample injection may also be carried out using an autosampler.

Hydrogen-containing samples which can be measured by means of the method according to the invention are liquid or gaseous inorganic and organic substances such as water, ammonia, hydrogen sulfide, alcohols and fruit juices, components of natural gas and petroleum, vegetable and animal (including human) metabolites as well as amino acids and fatty acids.

The major difference between the reduction oven of the invention and familiar reduction ovens which essentially consist of a pipe, is the capillary 3. The capillary should have a volume as small as possible in order to prevent isotope fractionating during sample evaporation, which would distort the measurement result. On the other hand, the capillary must be of such a length that the injection unit 1 will not be caused to leak by the temperatures of more than 700° C. that are present in the reaction chamber 4. The temperature at the injection unit must be about 150° C., ensuring flash evaporation of the sample.

With respect to its size, the reaction chamber 4 of the oven must represent the optimum in sample passage, measuring correctness and constancy of temperature. It appeared that a sample passage of 100 to 150 samples of 1 μl of water each (or hydrogen equivalent) requires a reaction chamber of between 50–60 mm in length and 15–20 mm internal diameter (ID). As a consequence, with an internal diameter between 0.6–1 mm, the length of the capillary should be between 50–100 mm.

Figure 3:
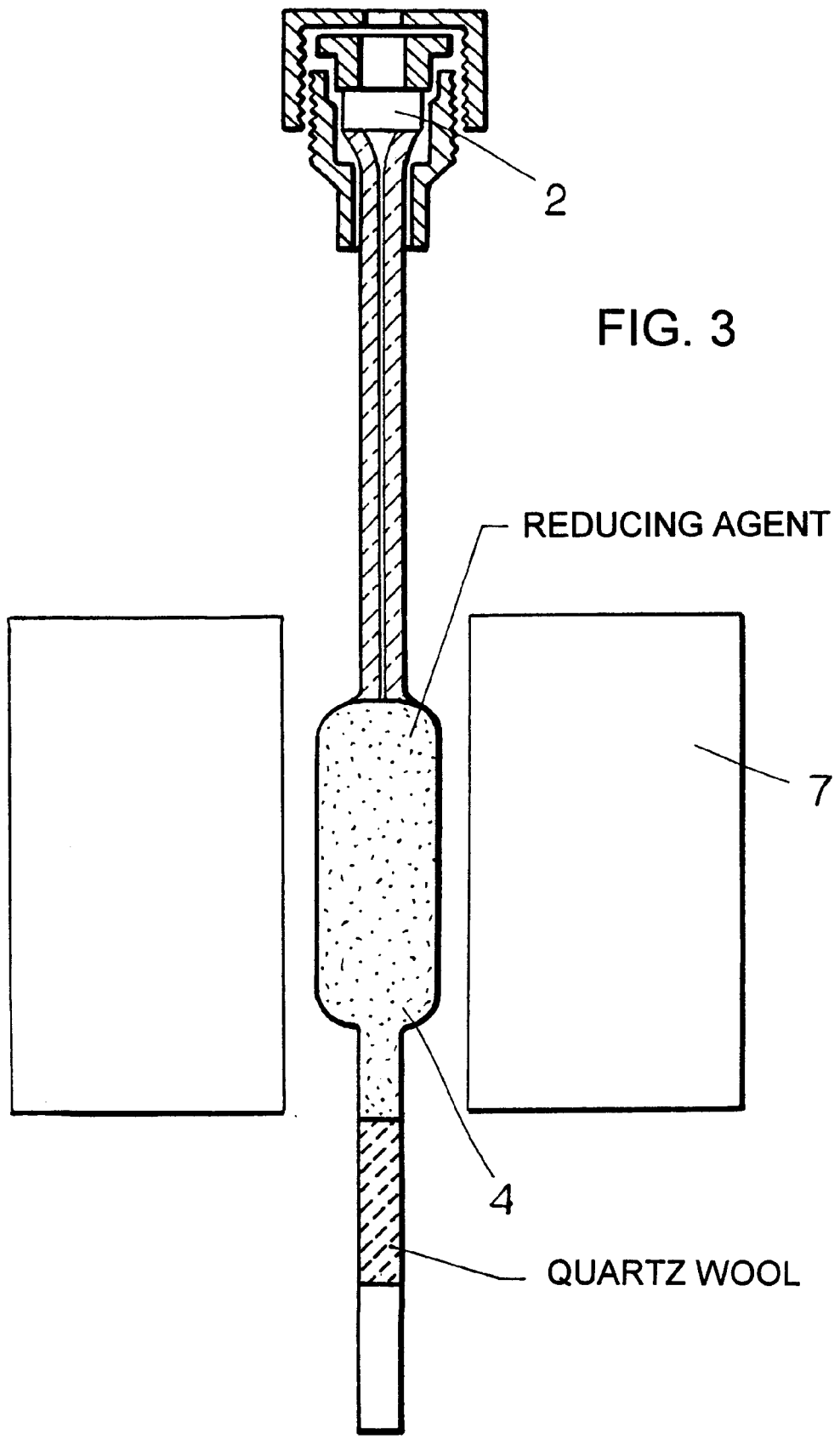
FIG. 3 is a further embodiment of the reduction oven of the invention.

In a particularly preferred embodiment of the invention, the reduction oven according to FIG. 3 is used. This oven has a capillary of 100 mm in length and 0.8 mm ID. The reaction chamber is 50 mm in length and has an ID of 16 mm (outside diameter=OD=18 mm).

The joint pipe 90 mm in length (¼" OD, MS-compatible) has quartz wool inside. In that section of the joint pipe, which is charged with chromium so far but is not part of the temperature-constant reaction chamber, all the other elements possibly contained in the sample are bound by chromium.

The capillary of the reduction oven illustrated in FIG. 3 has an internal volume of about 0.05 ml. The free volume in the reaction chamber charged with chromium is about 3 ml. The connecting pipe extending from the outlet of the reaction chamber up to and including the bellow has a volume of about 45 ml. This ratio of about 1:15 between the free volume of the charged reaction chamber (including the capillary) and the volume of the bellow (including connecting pipe) was found to be the optimum ratio in order to keep the measuring error as small as possible.

The advantages of the method according to the invention using the reduction oven of the invention are obvious and will be illustrated once again in summary below:

working with exceedingly small quantities of sample ($\leq 1$ mg of water or hydrogen equivalent) is possible, thereby permitting the use of the deuterium determination in fields such as geology (rock inclusions), microbiology, medicine or biochemistry;

utilization of the more accurate measuring method of position measurement of the isotope ratio by sample/standard comparison in the IRMS;

high measuring accuracy: standard deviation=$\pm 1$‰;

exceedingly simple set-up of apparatus;

ready for measurement in a short time, high reliability, simple handling in use and maintenance;

the quartz oven is quickly prepared to be re-used by simply changing the reducing agent;

the process can be automated (injection using an autosampler);

direct measurement of the deuterium content of most various natural substances without previous conversion to water.

In the following, the performance of the online method of the invention will be illustrated using two embodiments which are not limiting the method of the invention.

EXAMPLE 1

Determination of the Deuterium Content in Standard Waters

The new reduction oven of the invention according to FIG. 3 is charged with commercially available chromium powder (grain size $\leq 0.3$ mm) and heated under vacuum to the required temperature which is 900° C. for water. The injection site is sealed from external air using a septum. The sample (1 µl of water) is injected using a vacuum-tight microliter syringe. The syringe needle is placed in the vacuum of the hot oven for about 20 seconds, thus removing adhering water. In this way, it is ready to be used for injecting another sample without washing.

The evaporating water is reduced and, due to the pressure difference between the reduction oven and the bellow of the inlet element, the hydrogen formed flows into the mass spectrometer. Following pressure balancing (about 20 s), the inlet valve to the variable volume is closed, and the measurement begins.

Prior to measurement, the intensities of the mass 2 measured signals of the hydrogen gas from sample and standard are adjusted by the IRMS.

Thereafter, the isotope ratio D/H is measured in sample/standard alternation, and the $\delta$D value of the sample is calculated, which is accomplished using the following formula:

$$\delta(‰) = \frac{R_{Sample} - R_{Standard}}{R_{Standard}} \cdot 10^3$$

wherein R represents the isotope ratio D/H which is measured by means of the method according to the invention.

For testing the described method, the standard waters of the International Atomic Energy Agency (IAEA) are used:

V-SMOW: according to definition $\delta=0$‰

SLAP: according to definition $\delta=-428$‰ relative to SMOW

GISP: according to definition $\delta=-189.65\pm1.82$‰ relative to SMOW-SLAP

|  | SMOW $\delta= 0$‰ | GISP $\delta= -189.9$‰ | SLAP $\delta= -428$‰ |
|---|---|---|---|
| 1st Series of measurements | | | |
| Mean value $\delta$ | 3.3 | -186.9 | -422.9 |
| s (standard deviation) | 0.75 | 0.1 | 0.35 |
| n (number of determinations) | 7 | 2 | 4 |
| Standardization | | | |
| against SMOW | 0 | -189.6 | -424.8 |
| against SMOW-SLAP | 0 | -190.9 | -428 |
| 2nd Series of measurements | | | |
| Mean value $\delta$ | 0.73 | -187.6 | -425.7 |
| s (standard deviation) | 1.15 | 0.77 | 0.97 |
| n (number of determinations) | 6 | 5 | 6 |
| Standardization | | | |
| against SMOW | 0 | -188.2 | -426.1 |
| against SMOW-SLAP | 0 | -189.1 | -428 |

The results show that the online method according to the invention provides correct values.

EXAMPLE 2

Deuterium determination according to the invention on various samples Comparison between the offline method and the method according to the invention

| Samples | $\delta$D values [‰] offline | $\delta$D values [‰] direct coupling | n | Standard deviation [‰] direct coupling |
|---|---|---|---|---|
| MAOW (Middle Atlantic ocean water) | +0.7 | +0.5 | 10 | 1.2 |
| Precipitation sample | -100.8 | -100.1 | 10 | 1.4 |
| Antarctic Precipitation | -290.4 | -289.8 | 10 | 1.1 |
| Natural gas-associated saline water* | -67.4 | -66.9 | 5 | 0.7 |
| Champagner 1 | -8.1 | 7.9 | 3 | 0.4 |
| Champagner 2 | -1.2 | -0.8 | 3 | 0.7 |
| Methane | -162.6 | -162.6 | 5 | 1.1 |

*Salt content: 24,700 mg/l Na, 1,039 mg/l Ca, 385 mg/l Mg, 37,750 mg/l Cl⁻, 5,300 mg/l $SO_4^{2-}$ The results show that the method of the invention ovides correct and reproducible values in various applitions.

List of Reference Numbers

FIG. 1
1 Injection unit
2 Septum
3 Capillary
4 Reaction chamber
5 Joint pipe
6 Temperature-resistant material confining the reaction chamber
7 External heating device
FIG. 3
All figures in mm

What is claimed is:

1. A method for quantitative deuterium determination in hydrogen-containing samples by direct coupling of a reduction oven to an isotope ratio mass spectrometer (IRMS), wherein hydrogen gas is liberated from the hydrogen-containing sample by reduction, comprising the steps of providing chromium as reducing agent in a reaction chamber of a reduction oven, evacuating and heating the reduction oven by means of an external heating device to a temperature which must be at least 700° C. in the reaction chamber and about 150° C. at an injection site, injecting the hydrogen-containing sample into the oven, evaporating the sample instantaneously and forming hydrogen gas by reduction of the sample on the chromium, whereby said hydrogen gas flows into the isotope ratio mass spectrometer because of the pressure difference between the reduction oven and a variable volume bellow of an inlet element of the mass spectrometer, closing the inlet element to the isotope ratio mass spectrometer subsequent to pressure balancing, and measuring the isotope ratio D/H of the sample.

2. The process according to claim 1, further comprising providing an autosampler for injecting the samples.

3. The process according to claim 1, wherein a catalyst selected from the group consisting of nickel, platinum, cobalt, tungsten and molybdenum or a mixture thereof is added to the chromium.

4. The process according to claim 3, wherein the ratio of chromium and catalyst is between 100:1 and 20:1.

5. The process according to claim 1, wherein the chromium is employed as chromium powder having a grain size of from 0.16–0.3 mm.

6. The process according to claim 5, wherein a catalyst selected from the group consisting of nickel, platinum, cobalt, tungsten and molybdenum or a mixture thereof is added to the chromium.

7. The process according to claim 6, wherein the ratio of chromium and catalyst is between 100:1 and 20:1.

* * * * *